US008932234B2

(12) United States Patent
Peters et al.

(10) Patent No.: US 8,932,234 B2
(45) Date of Patent: Jan. 13, 2015

(54) DEVICES, SYSTEMS, AND METHODS FOR THE COLLECTION OF BODY FLUIDS

(75) Inventors: Scott R. Peters, West Lafayette, IN (US); James M. Hampsch, Lafayette, IN (US)

(73) Assignee: Bioanalytical Systems, Inc., West Lafayette, IN (US)

( * ) Notice: Subject to any disclaimer, the term of this patent is extended or adjusted under 35 U.S.C. 154(b) by 192 days.

(21) Appl. No.: 13/270,902

(22) Filed: Oct. 11, 2011

(65) Prior Publication Data

US 2012/0088250 A1    Apr. 12, 2012

Related U.S. Application Data (60) Provisional application No. 61/391,856, filed on Oct. 11, 2010.

(51) Int. Cl.
A61B 5/00 (2006.01)
A61B 5/155 (2006.01)
B01L 3/00 (2006.01)
A61B 10/00 (2006.01)
A61B 5/15 (2006.01)
G01N 35/00 (2006.01)
G01N 1/28 (2006.01)

(52) U.S. Cl.
CPC ............... *A61B 5/1427* (2013.01); *B01L 3/50* (2013.01); *B01L 3/5085* (2013.01); *B01L 3/50853* (2013.01); *A61B 10/0096* (2013.01); *A61B 5/150358* (2013.01); *A61B 5/155* (2013.01); *A61B 5/1405* (2013.01); *B01L 2300/0803* (2013.01); *B01L 2300/0806* (2013.01); *G01N 35/00069* (2013.01); *G01N 2001/2826* (2013.01); *G01N 2001/288* (2013.01); *A61B 5/15003* (2013.01)

USPC ............ 600/575; 73/61.55; 73/863; 422/420; 422/548; 422/551; 422/552; 422/939; 435/287.7; 435/287.8; 435/287.9

(58) Field of Classification Search
USPC .......... 73/863, 863.33, 864.91; 206/569, 570, 206/461, 462, 464, 467, 231, 775, 781; 422/420, 548, 551, 552, 939; 435/287.7–287.9; 600/573, 575; 604/6.15, 403

See application file for complete search history.

(56) References Cited

U.S. PATENT DOCUMENTS

| 5,516,487 A | * | 5/1996 | Rosenthal et al. | 422/420 |
| 2003/0170143 A1 | * | 9/2003 | Cunningham | 422/57 |
| 2004/0265187 A1 | * | 12/2004 | Davin | 422/102 |
| 2005/0084422 A1 | * | 4/2005 | Kido et al. | 422/100 |
| 2011/0077480 A1 | * | 3/2011 | Bloom et al. | 600/310 |

* cited by examiner

*Primary Examiner* — Melanie Y Brown
*Assistant Examiner* — Erik B Crawford
(74) *Attorney, Agent, or Firm* — Ice Miller LLP (57) ABSTRACT

Devices, systems, and methods for the collection of biological samples. In at least one exemplary embodiment, a device comprises a collection medium having top and bottom surfaces and a predetermined size and shape, the top surface comprising a position marker and at least one binding site operable to bind a biological sample, a protective facing substantially impermeable to the biological sample, the protective facing coupled to the top surface of the collection medium and having a size and shape substantially similar to the predetermined size and shape of the collection medium. The protective facing being sized and shaped to define a first void positioned to allow for the transfer of the biological sample through the protective facing and onto the at least one binding site of the collection medium, and a second void positioned to expose the position marker for alignment of the collection medium.

23 Claims, 11 Drawing Sheets

Section A-A

Fig. 5

Section A-A

Fig. 6

Section A-A

DEVICES, SYSTEMS, AND METHODS FOR THE COLLECTION OF BODY FLUIDS

CROSS REFERENCE TO RELATED APPLICATIONS

The present U.S. utility patent application is related to and claims the priority benefit to U.S. Provisional Patent Application Ser. No. 61/391,856, filed Oct. 11, 2010, the contents of which are hereby incorporated by reference in their entirety into this disclosure.

BACKGROUND

In laboratory and clinical settings, it is often necessary to take, contain, transport, and store biological samples, such as blood or blood products, to determine the concentration of various components in the sample. The analysis of biological fluids to confirm the levels or concentrations of various components contained therein is an accepted clinical practice for the determination of the pharmacokinetic properties of drug compounds in the bloodstream.

Conventional liquid sample collection, handling, transport, and storage, in a glass or plastic tube, has many problems associated with it, including: (1) the risk of container breakage or leakage which causes loss of sample and the danger of infection to the handlers; (2) sample instability during shipment and storage; (3) refusal of transport carriers to accept liquid biohazardous shipments, (4) requiring the collection of more sample than is necessary for testing, to ensure quantities compatible with common laboratory methods of serum or plasma preparation and subsequent analysis, and (5) the fact that limited quantities of fluid available for extraction from small animals such as mice and rats do not allow enough serial liquid samples to be collected from each animal.

In the case of certain blood component determinations, the handling of the blood samples can also be a critical part of the ultimate accuracy of measurement in the sample. Therefore, even when a blood sample is removed from the body, the concentration of the component within a liquid blood sample can change over time.

To overcome these problems, in one approach, a biological sample, e.g., a drop or two of whole blood is collected on collection media such as specially manufactured paper and dried prior to transport. These dried blood spot (DBS) samples can be obtained using small amount of blood (typically 15 μL-20 μL), can be mailed and are accepted by all common carriers. Dried blood spots have the advantage of helping to preserve certain components for later analysis.

The extraction of blood and deposition of blood spots from test subjects onto suitable media such as a collection media is generally labor intensive and requires skill to accurately pipette and dispense blood onto paper without causing separation of blood components as the blood disperses on the paper. Inconsistent deposition of blood can produce variation in subsequent analysis of DBS samples.

Further, manual dispensing of spots onto cards may not accurately position the sample. The variation from manual positioning creates difficulties for subsequent automation used to punch blood spots from cards or analyze the spots directly, as it requires specialized instrumentation that must first identify the location of the blood spot before processing. This requirement introduces considerable complexity to the instrumentation and introduces reliability issues to the proper analysis of misplaced blood spots.

Typically, pre-clinical pharmacokinetic studies require from eight (8) to twelve (12) serial blood samples taken at specified time points during a 24 hour period. For each time point, one (1) to four (4) dried blood spots are collected. Commercially available dried blood spot cards for bioanalytical analysis hold up to 4 dried blood spots each. One (1) card is used for each time point. After collection of the blood onto the card the blood must be allowed to dry for a minimum of two (2) hours. Space must be available for air circulation around the card to allow each liquid sample to dry. When large numbers of test subjects are being sampled, the large number of blood spot cards generated requires significant physical space to separate cards for drying the blood spots. Each individual card must be labeled for subject identification and identification of the time point for that subject.

SUMMARY

In at least one embodiment of a storage device for biological samples of the present disclosure, the device comprises a collection medium having a top surface, a bottom surface, and a predetermined size and shape, the top surface comprising a position marker and at least one binding site operable to bind a biological sample. The exemplary device further comprising a protective facing substantially impermeable to the biological sample, the protective facing coupled to the top surface of the collection medium and having a size and shape substantially similar to the predetermined size and shape of the collection medium, wherein the protective facing is sized and shaped to define a first void an a second void, the first void positioned to allow for the transfer of the biological sample through the protective facing and onto the at least one binding site of the collection medium, the second void positioned to expose the position marker for alignment of the collection medium. The collection medium of the storage device may optionally be circular in at least one embodiment. Further, the storage device may also comprise an identification marker coupled to the protective facing.

In at least one embodiment of the device of the present disclosure, the at least one binding site is positioned proximate to an edge of the collection medium. Further, the at least one binding site may comprise a plurality of binding sites each positioned in a row along the edge of the collection medium.

In at least one embodiment of the device of the present disclosure, the collection medium further comprise a separation element operable to divide the collection medium into at least two predetermined portions. An exemplary separation medium may include a perforation capable of separating the collection medium into the at least two predetermined portions upon exertion of a force. Further, the separation element may be positioned so as to divide the collection medium into the at least two predetermined portions through the position marker.

In at least one embodiment of the device of the present disclosure the biological sample is selected from the group consisting of blood, blood fractions, sweat, urine, tears and cerebral spinal fluid, or combinations thereof.

In at least one embodiment of the device of the present disclosure, the collection medium and protective facing are each shaped to define a first alignment void and a second alignment void respectively; the first alignment void and second alignment void being structured and positioned so as to allow the passage of an alignment member through each.

In at least one embodiment of the device of the present disclosure, the protective facing comprises a coupling member and the protective facing is shaped to define a coupling void capable of engaging the facing coupling member. Optionally, the protective facing may comprises a top facing and a bottom facing where the top facing shaped to define the coupling void and the bottom facing defining the coupling member, wherein when the collection medium is placed between the top facing and bottom facing, and the coupling void engages the coupling member, the collection medium is securably engaged to the protective facing.

In at least one embodiment of the device of the present disclosure, the device may further comprise an alignment member traversing both the first alignment void and second alignment void, and securing the collection medium to the protective facing.

In at least one embodiment of the device of the present disclosure, the position marker defines a channel between the top and bottom surface of the collection medium.

In at least one embodiment of the device of the present disclosure, the protective facing is coupled to a top surface of the collection medium.

In at least one embodiment of the device of the present disclosure, the storage device is sized and shaped to define at least one alignment void operable for engaging a sample collection apparatus.

In at least one embodiment of a system for the storage of biological materials of the present disclosure, the system comprises a biological sample collection apparatus capable of collecting a biological sample from a subject, and an embodiment of a storage device of the present disclosure.

In at least one embodiment of a system of the present disclosure, the at least one binding site is positioned proximate to an edge of the collection medium. The at least one binding site comprises a plurality of binding sites each positioned in a row along the edge of the collection medium.

An exemplary embodiment of the collection medium of the present disclosure may also comprise a separation element operable to divide the collection medium into at least two predetermined portions. Further, the separation element may be a perforation capable of separating the collection medium into the at least two predetermined portions upon exertion of a force. Additionally, the separation element may be positioned so as to divide the collection medium through the position marker.

In at least one embodiment of a method for storage of biological samples of the present disclosure, the method comprises the steps of (1) coupling an embodiment of a storage device of the present disclosure to a biological sample collection apparatus capable of collecting a biological sample from a subject, (2) introducing a biological sample from the biological sample collection apparatus to at least one binding site of the collection medium, and (3) drying the biological sample on the collection medium. In an exemplary embodiment of the method, the at least one binding site is positioned proximate to an edge of the collection medium. The at least one binding site may also a plurality of binding sites each positioned in a row along the edge of the collection medium. An exemplary embodiment of the method of the present disclosure may further comprise the step of introducing a duplicate biological sample to a second binding site of the at least one binding site of the collection medium.

BRIEF DESCRIPTION OF THE DRAWINGS

The features and advantages of the present disclosure, and the manner of attaining them, will be more apparent and better understood by reference to the following descriptions taken in conjunction with the accompanying figures, wherein.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 1:
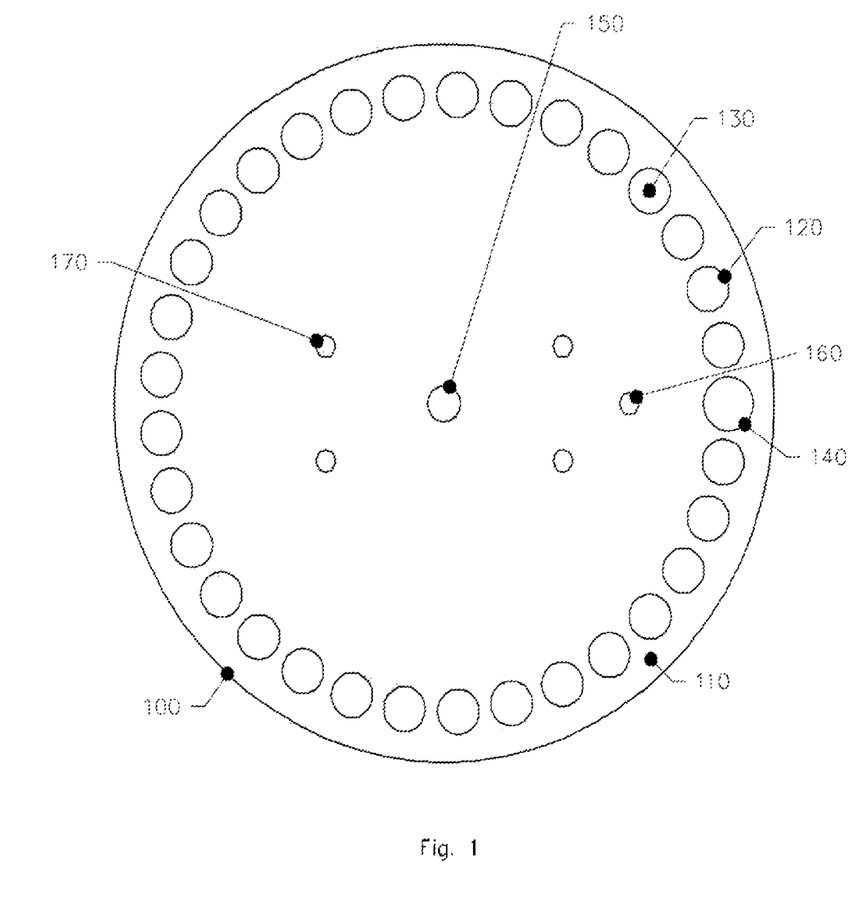
FIG. 1 shows a top plan view of a card assembly, according to at least one embodiment of the present disclosure.

According to FIG. 1, a sample collection device is disclosed, which contains biological samples such as dried blood spot samples, and can be used with existing sampling instruments. For example, a single device (such as a card), which accepts all of the blood spots from a complete pharmacokinetic time series is disclosed. Such an exemplary embodiment of a device of the present disclosure may greatly reduce the space and labeling requirements for completing a study. Additionally, the number of devices handed, stored, tracked, and shipped may be reduced through the use of such an embodiment.

In FIG. 1, a top plan view of at least one embodiment of sample collection device (also referred to herein as card assembly) 100 is shown. The top facing 110 includes facing holes 120 equally spaced on a circle diameter near the periphery of the card exposing collection medium 130. Facing hole 120 may define the position and size of sample spot 135 on collection medium 130. The bottom facing 180 (not shown) has holes which align with the holes of the top facing so that collection medium is exposed on the top and bottom at the same locations. A home position 140 is at one location on the same circle diameter equally spaced from the blood spot locations. At this home position 140 there is no collection medium and the hole is clear through top facing 110, collection medium 130, and bottom facing 180. The size of this hole may be larger than the sample spot location. Hole 150 in at least one embodiment is located in the center of the disk and passes clear through top facing 110, collection medium 130, and bottom facing 180. Hole 160 is an alignment hole for the entire card assembly and passes through all layers of the card.

Four or more holes 170 are used for alignment of card halves if the card is cut in two halves. These holes pass through all layers of the card.

Figure 2:
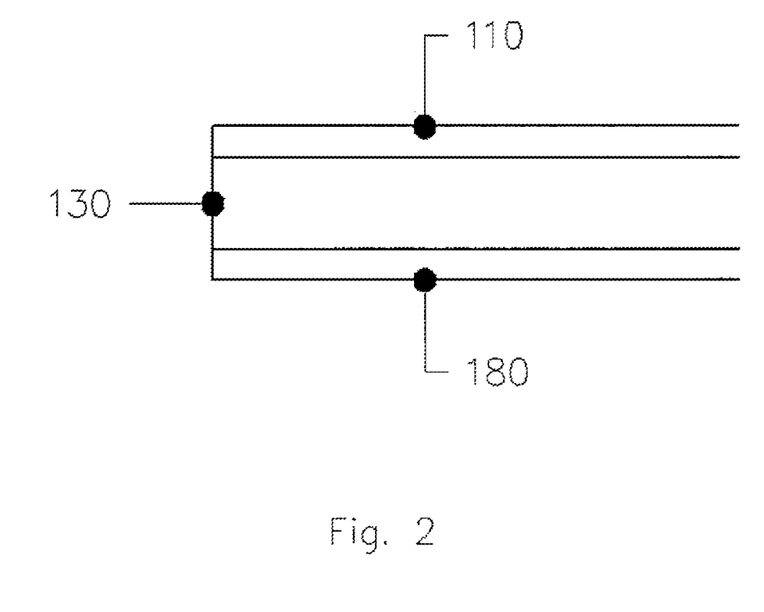
FIG. 2 shows an expanded side plan view of an embodiment card assembly FIG. 1, according to at least one embodiment of the present disclosure.

FIG. 2 shows an expanded side view of the edge of an embodiment of card assembly 100 illustrating a sandwich of top facing 110, collection medium 130, and bottom facing 180.

Figure 3:
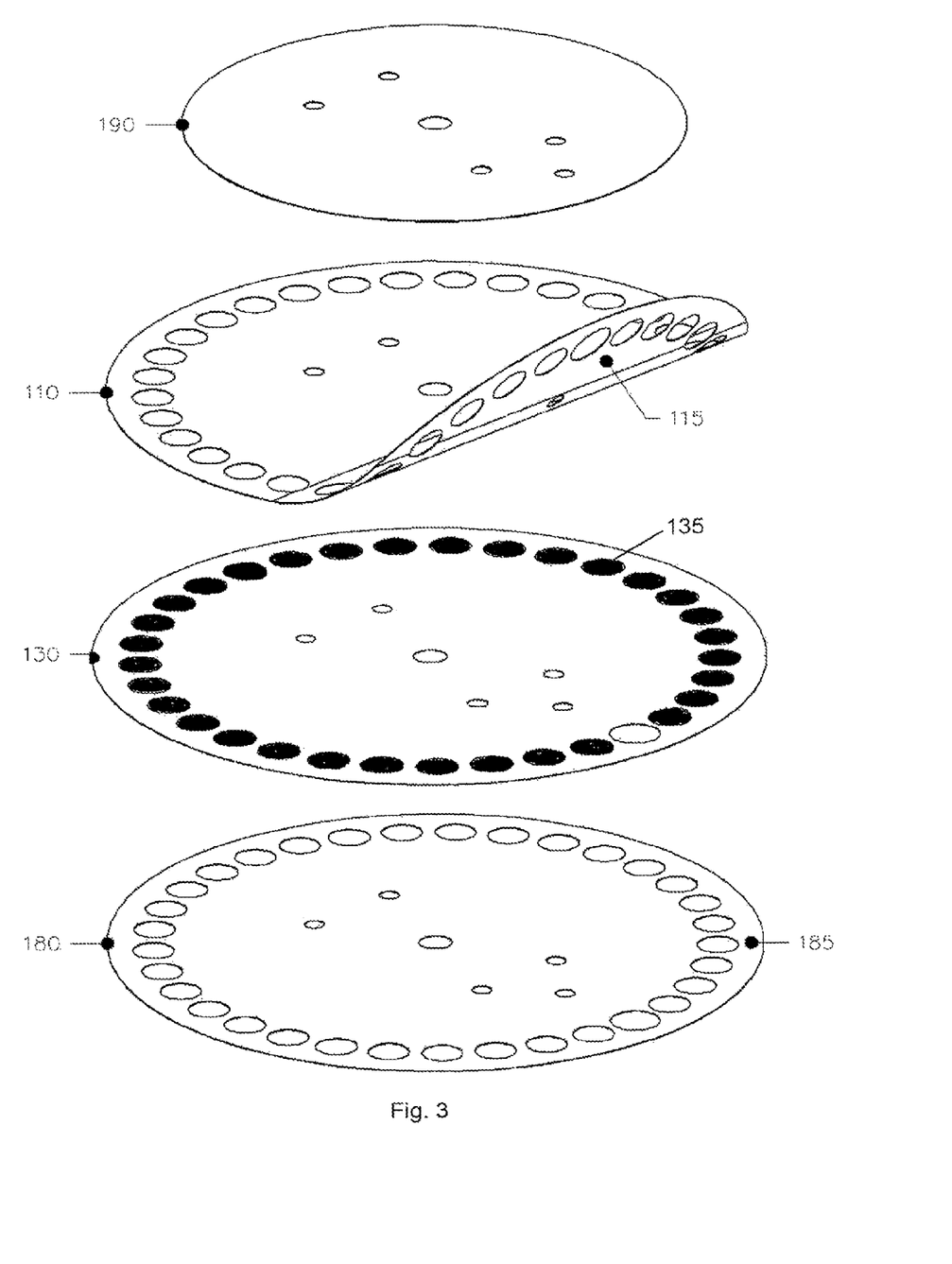
FIG. 3 shows an exploded side perspective view of a card assembly of FIG. 1, according to at least one embodiment of the present disclosure.

FIG. 3 shows an exploded view of an embodiment of card assembly 100. Top facing 110 and bottom facing 180 include all holes 120, 140, 150, 160, and 170 (as shown in FIG. 1). The collection medium 130 may also include holes 140, 150, 160 and 170. The facing 110 in at least one exemplary embodiment has adhesive covering the entire face 115 of one side of facing 110, which contacts and bonds to the collection medium 130. Facing 180 may also have adhesive covering the entire face on one side 185 which contacts and bonds to the collection medium. According to an exemplary embodiment, adhesive backed label 190 may further comprise at least one identification element, such as graphics for identifying the study and location number, the label 190 contacts and bonds to the top facing 110. The label 190 may also include holes 150, 160, and 170.

Figure 4:
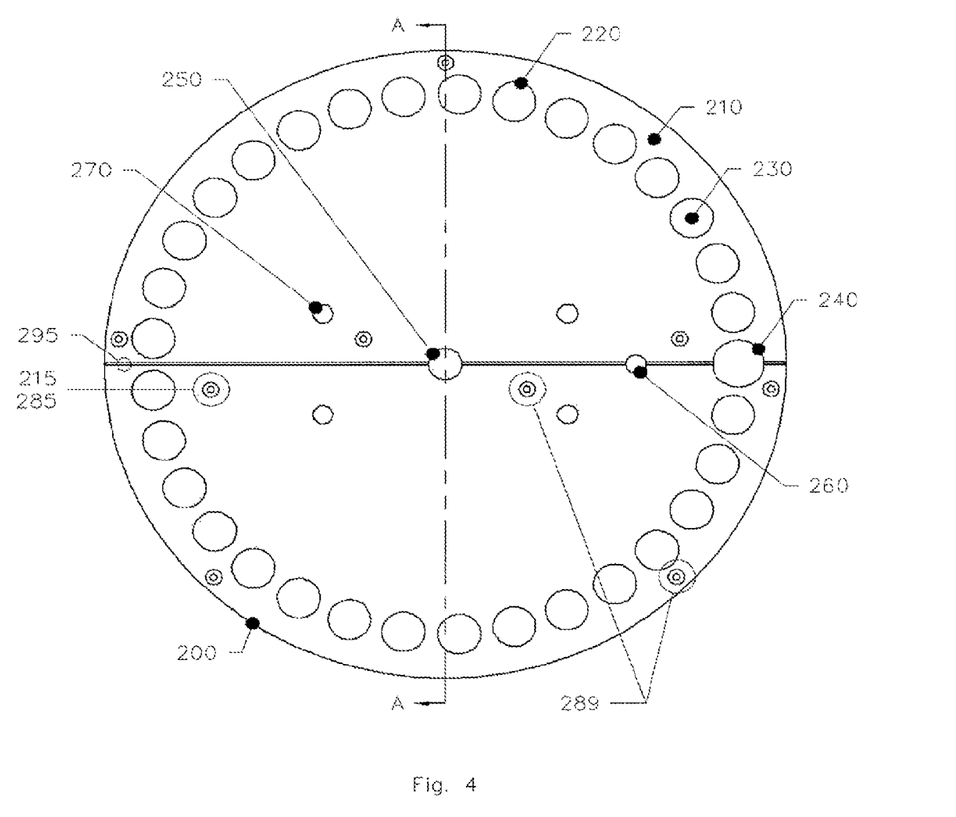
FIG. 4 shows a top plan view of a card assembly, according to at least one embodiment of the present disclosure.

FIG. 4 shows a top view of an embodiment of the card assembly 200, with elements 210, 220, 230, 240, 250, 260, and 270 corresponding to elements 110, 120, 130, 140, 150, 150, 160, 170 of FIG. 1 respectively. Exemplary card assembly 200 may also comprise a bottom facing 280 in at least one embodiment. An embodiment of card assembly 200 may use a mechanical mechanism such as mechanical fasteners 289 to attach the assembly together. In an exemplary embodiment, the mechanical fasteners 289 are located near the outer periphery and on both sides of a notch 295 extending along the center of the card. The notch 295 in top facing 210 passes through alignment holes 260 and 250 and extends the entire width of the card. A matching notch 297 is located on the bottom facing 280 (not shown).

Figure 5:
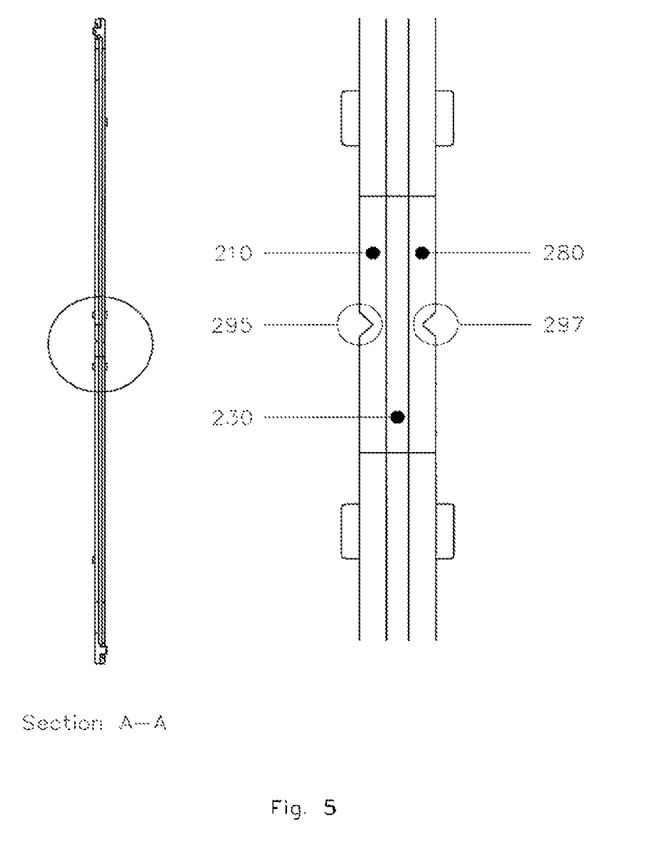
FIG. 5 shows a cross-sectional view of the card assembly of FIG. 4 taken along axis A-A, according to at least one embodiment of the present disclosure.

FIG. 5 shows a cross sectional view of FIG. 4 along line A-A illustrating the top facing 210 and bottom facing 280 enclosing paper 230 which is a smaller diameter than the facings. Notches 295 and 297 are aligned with each other and enable the card to be cut into two equal halves using common cutting tools such as scissors.

Figure 6:
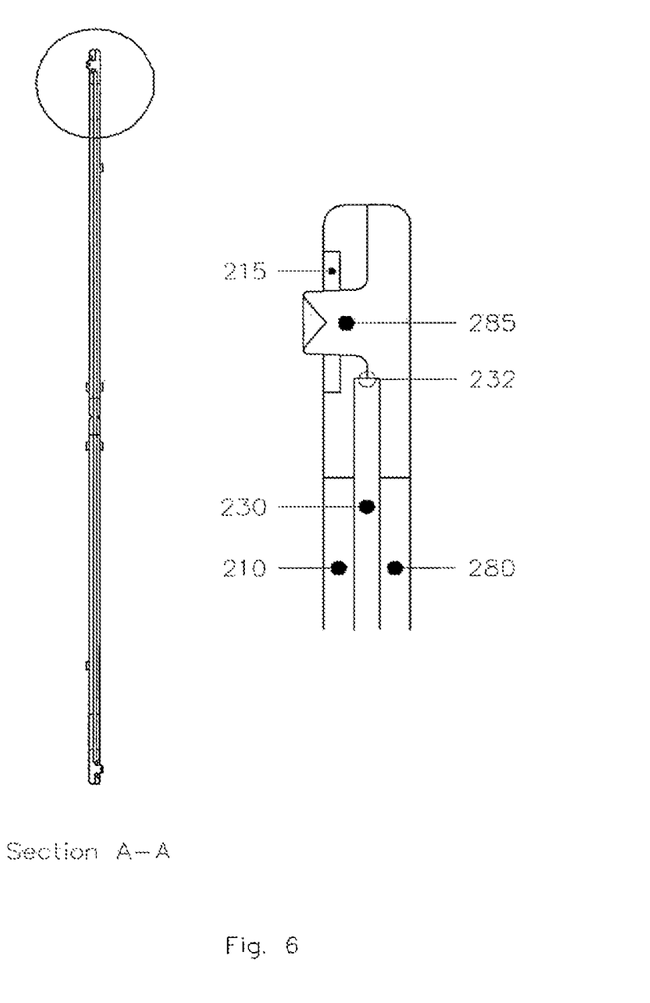
FIG. 6 shows an expanded partial cross-sectional view of a card assembly of FIG. 4 taken along axis A-A, according to at least one embodiment of the present disclosure.

FIG. 6 shows an expanded partial cross sectional view of an exemplary card assembly 200 at the outside edge. Male fasteners 285 in the bottom facing 280 pass through holes 215 in the top facing and are deformed to lock the top and bottom facings together, sandwiching the collection medium 230 and enclosing the outer edge 232 of the collection medium between.

Figure 7:
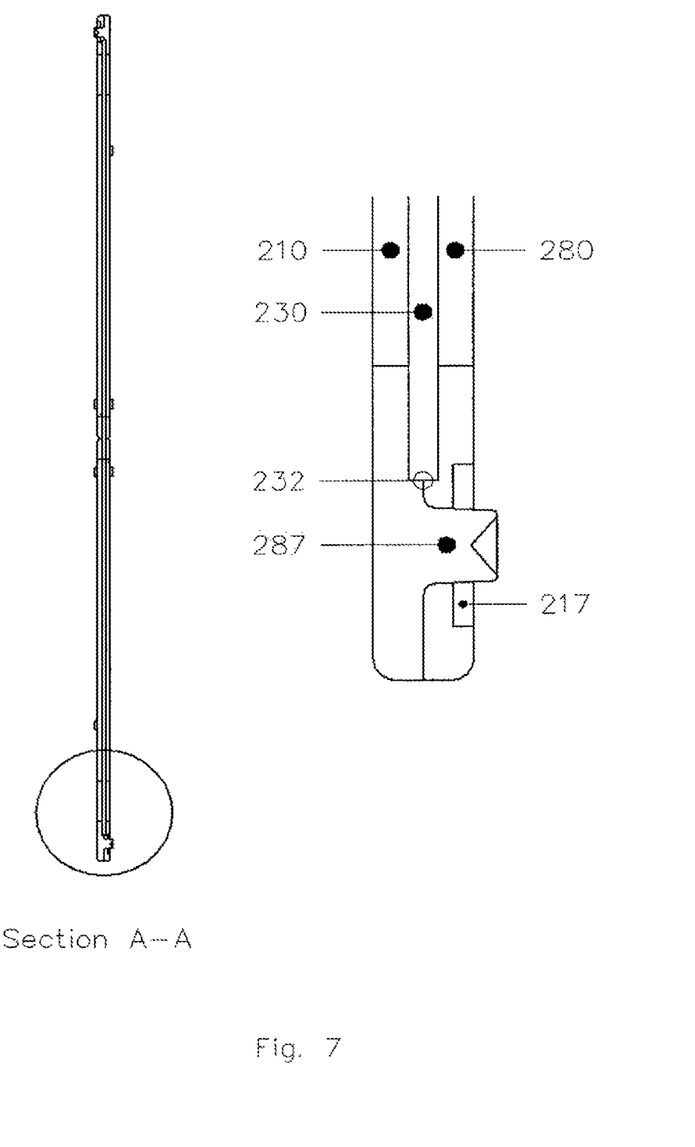
FIG. 7 shows an expanded partial cross-sectional view of a card assembly of FIG. 4 taken along axis A-A, according to at least one embodiment of the present disclosure.

FIG. 7 shows an expanded partial cross sectional view of an exemplary card assembly 200 at the outside edge. In a manner similar to that shown in FIG. 6, male fasteners 287 in the top facing 210 pass through holes 217 in the bottom facing and are deformed to lock the top and bottom facings together, sandwiching the collection medium and enclosing the outer edge of the paper between.

Figure 8A:
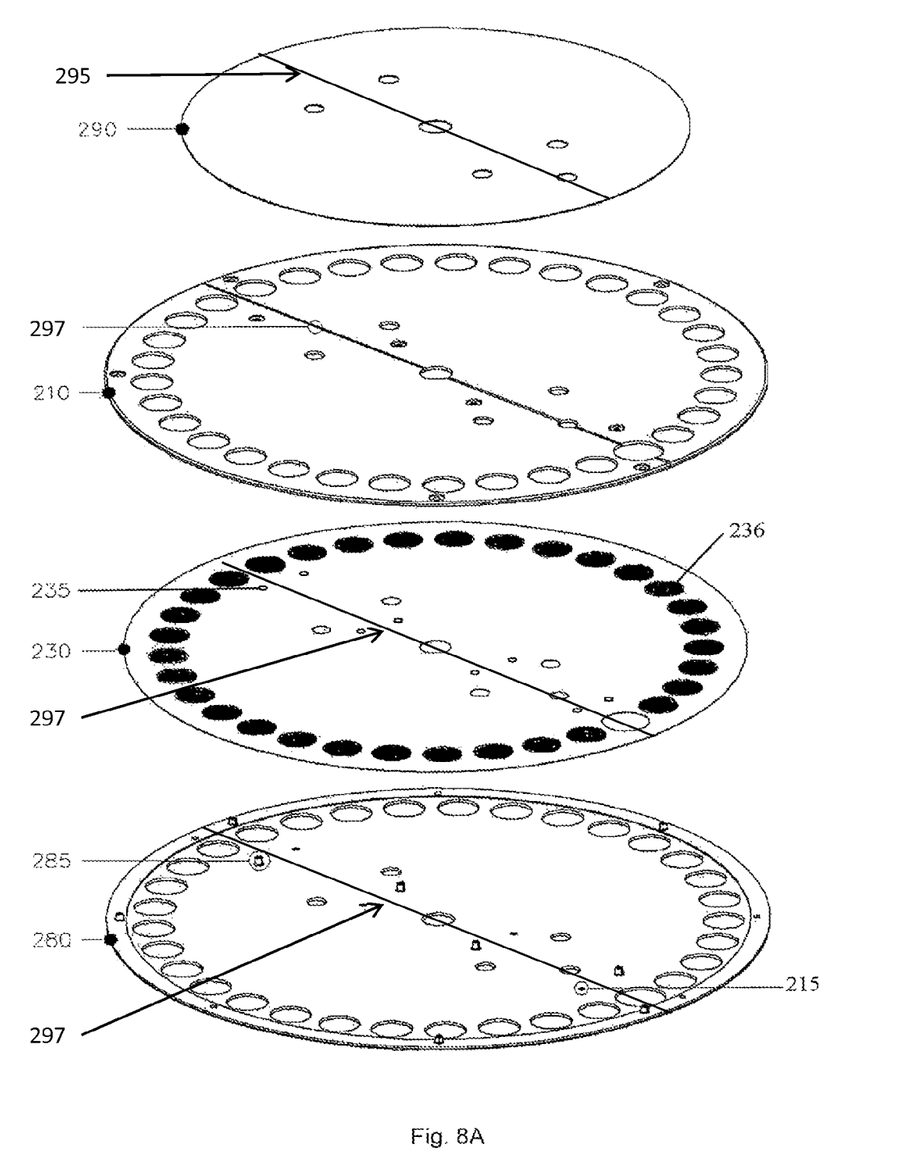
FIG. 8A shows an exploded side perspective view of a card assembly of FIG. 4, according to at least one embodiment of the present disclosure.

FIG. 8A shows an exploded view of an embodiment of the card assembly 200. An adhesive backed label 290 attaches to the top of the top facing 210. The exemplary top facing has holes for spot locations and alignment as well as pins 285 and holes 215 for mechanical attachment. The collection medium includes alignment holes 250, 260, 270, home position hole 240 and holes 235 to allow central facing pins to pass through. At least one exemplary bottom facing 280 also includes pins where holes are found in top facing 210 and has holes at locations where top facing 210 has pins to provide alignment and/or coupling of the elements of the card assembly.

In at least one embodiment of the present disclosure, male fastener 285 and/or 287 may be referred to a coupling member or a facing coupling member, and holes 215 and/or 217 may be referred to as a coupling void or facing coupling void.

At least one embodiment of the present disclosure relates to a storage device 100 for biological samples, wherein the storage device 100 comprises a collection medium 130 capable of binding a biological sample and a protective facing 110 and/or 180 that are substantially impermeable to the biological sample, where the protective facing 110 and/or 180 is coupled to at least one face of the collection medium 130. The protective facing 110 and/or 180 may also be sized and shaped to define a least one sample void sufficient for the flow of the biological sample therethrough. Further, the protective facing 110 and/or 180 and collection medium 130 may also be sized and shaped to define at least one alignment void 160 capable of being engaged by a sample collection apparatus.

The device 100 may be used with an automated sampling instrument for the collection of serial blood samples from test subjects. At least one embodiment of the device of the present disclosure may be referred herein as a card assembly.

In an exemplary embodiment of the storage device 100, the collection medium 130 may be in the shape of a disk, such as depicted in FIG. 1, with a central hole 150 and alignment holes 160 for accepting alignment pins. An additional hole 140 in the paper for a home position may be provided as well. The collection medium 130 may be comprised of any applicable material such as cotton fiber, or synthetic fiber capable of absorbing or containing a biological sample. Additionally, the collection medium 130 may have a consistent matrix structure suited for collecting dried blood spots in a consistent manner, such as found in Alhstrom 226 (Ahlstrom Filtration LLC) or GE Medical FTA DMPK C (GE Healthcare). Further, the collection medium 130 may be comprised of any blood spot collection paper approved by the Centers for Disease Control.

The disk or circular shape of an embodiment of the collection medium 130 may be suited to automated collection of blood spots 135 using rotary based collection instruments. The disk configuration may also enable large numbers of blood spots to be collected on a single card with all spots located near the edge of the paper. For example, in at least one embodiment of storage device 100 or 200, the collection medium 130/230 has at least 1, at least 2, at least 4, at least 8, at least 12, at least 16, at least 24, at least 32, and at least 62 binding sites for binding of a liquid sample, such as blood. The number and positioning of sample spots 135 may allow the card assembly to be used with semi-automated punching machines developed for smaller blood spot cards, such as the BSD 600 Duet (BSD Robotics).

The collection medium 130 may be covered on both top and/or bottom by a rigid or semi-rigid protective facing 110 and/or 180 in the same disk shape as the collection medium 130. The protective facing 110 and/or 180 may sandwich the collection medium 130 forming a three-part sample collection card 100 which may be bonded together or attached together by mechanical mechanism (such as elements 285 or 289). In at least one exemplary embodiment, the protective facing 110 and/or 180 has central hole 150 and at least one alignment hole 160 which can align with holes 140 in the collection medium 130. The protective facing 110 and/or 180 may be comprised of a material substantially impermeable to flow of the biological sample therethrough. In at least one embodiment, the protective facing 110 and/or 180 material is comprised of a polymer.

Figure 8B:
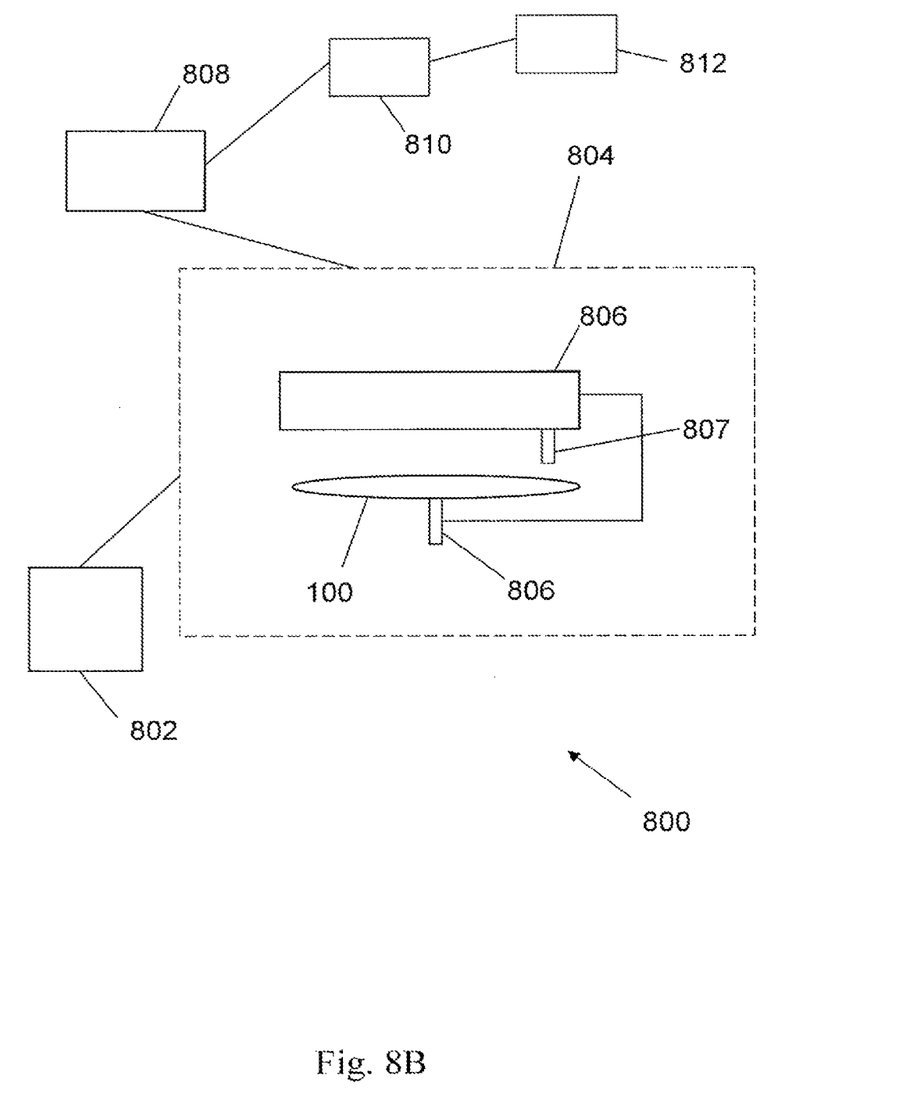
FIG. 8B shows a diagram of a system for sample collection, according to at least one embodiment of the present disclosure.

In at least one embodiment, protective facing 110 and/or 180 may comprise a series of facing holes 120. These holes which may be equally spaced circular holes near the periphery of the disk. Further, the facing holes 120 near the periphery of the disk of the top protective facing 110 align with the holes 120 near the periphery of the bottom protective facing 180. These facing holes 120 may expose sample spots 135 in the top and bottom surfaces of the collection medium 130 at these locations. Biological samples, such as blood spots, are deposited at these exposed sample spots 135 in the collection medium 130 locations. At least one purpose of the facing material can be to protect the collection medium 130 and sample spots 135 from contamination during normal handling of the card 100. The facing 110 and/or 180 may also provides rigidity to the card 100 to protect it from damage due to bending, edge contact damage, or folding. These distortions of the dried blood spot paper might cause difficulties for automated handling instruments post collection. The protective facing 110 and/or 180 may also rigidly support the collection medium 130 at a fixed distance below the dispensing needle 807 of automated blood collection instrument 800.

Spacing of the sample spots 135, in an embodiment of the sample device 100, along the outside periphery of the sample device 100 may facilitate the sample automation and card assembly registration to assure that blood spots may be processed accurately and reliably. Provisions for physically separating backup blood spots from those to be analyzed may be provided by depositing replicate spots on opposite sides of the card and separating the card in two halves after collection. Rigid facing 110 and/or 180 on both sides of the paper may protect the collection medium 130 and sample spots 135 from contamination and provides rigidity for automated handling and processing after collection.

According to at least one embodiment, the storage device 100 may comprise at least 2, at least 4, at least 8, at least 12, at least 16, at least 18, at least 20, at least 22, at least 24, at least 26, at least 28, at least 30, at least 32, at least 40, at least 50, at least 60, or at least 64 sample spots. An exemplary embodiment of the storage device 100 may comprise at least as many facing holes 120 as the number of sample spots 135.

In at least one embodiment of the storage device 100 or 200 of the present disclosure, the storage device may have a separation element 295 or 297, such as a notch, groove, perforation or other provision to allow it to be cut, broken, or ripped in equal halves along one direction by common cutting tools such as scissors, or through application of a force.

The storage device 100 or 200, in an exemplary embodiment, may further comprise an label 290, such as an adhesive backed label, which has alignment holes 160 or 260 matching those on the assembly card 100 or 200 provide identification for the sample spot 135 or 236 locations. The label 290 may also provide space for additional information, such as that specified by a user. In at least one embodiment, the label 290 provides an indication 295 where the card may be cut in half. Also, the label 290 may provide means to indicate if replicate samples are divided equally on opposite halves of the card or if a second series of blood spots are collected on the second half of the card. Further, as shown in FIG. 8A, an exemplary embodiment of storage device 100 or 200 may also have a separation member 297 in substantially identical positions on the collection medium 130 or 230 and the protective facing 110/180 or 210/280 as that of the indication 295 on label 290. Additionally, in an embodiment of storage device 100 or 200 where the collection medium 130/230 and protective facing 110/180 and/or 210/280 have a separation member 297, the indication 295 will have substantially the same characteristics as that of 297. For example, separation member 297 may be a perforation or other physical weakness which allows for separation of the storage device 100 or 200 into at least two predetermined portions upon exertion of a force. Such a separation may occur though the home position 140/240 and in some embodiments thorough an alignment hole 150/250.

In at least one embodiment, the card assembly 100 or 200 may have one or more spot locations in which collection medium is not present. At least one of these holes 140, which passes through the entire card assembly, is used as a 'home' position where the collection instrument needle resides when blood samples are not collected.

Systems for the collection and storage of bodily fluids may comprise a sampling component which is operable to collect a biological fluid from a subject, and deposit the sample onto at least one surface of an embodiment of the card assembly. Further, the system for the collection and storage of bodily fluids may further comprise an analysis component operable to analyze at least one component of the bodily fluid sample stored on the card assembly.

Turning to FIG. 8B a plan view of an embodiment of a system 800 for the storage of biological samples is shown. Exemplary system 800 comprises an embodiment of collection apparatus 802 capable of collecting a biological sample from a subject and a storage device 804 capable of receiving the biological sample from the collection apparatus 802, the storage device 804 comprising an embodiment of collection medium 130 and aliquoting device 806. An exemplary aliquoting device 806 may be fluidly coupled to an aliquoting needle 807 capable of delivering a fluid sample to collection material 130/230. Further, storage device 804 and/or collection device 802 may be in communication directly or through a network with controller 808 which may comprise one or more processor and database 810, and may additionally be in communication with one or more additional processor 812.

Figure 9:
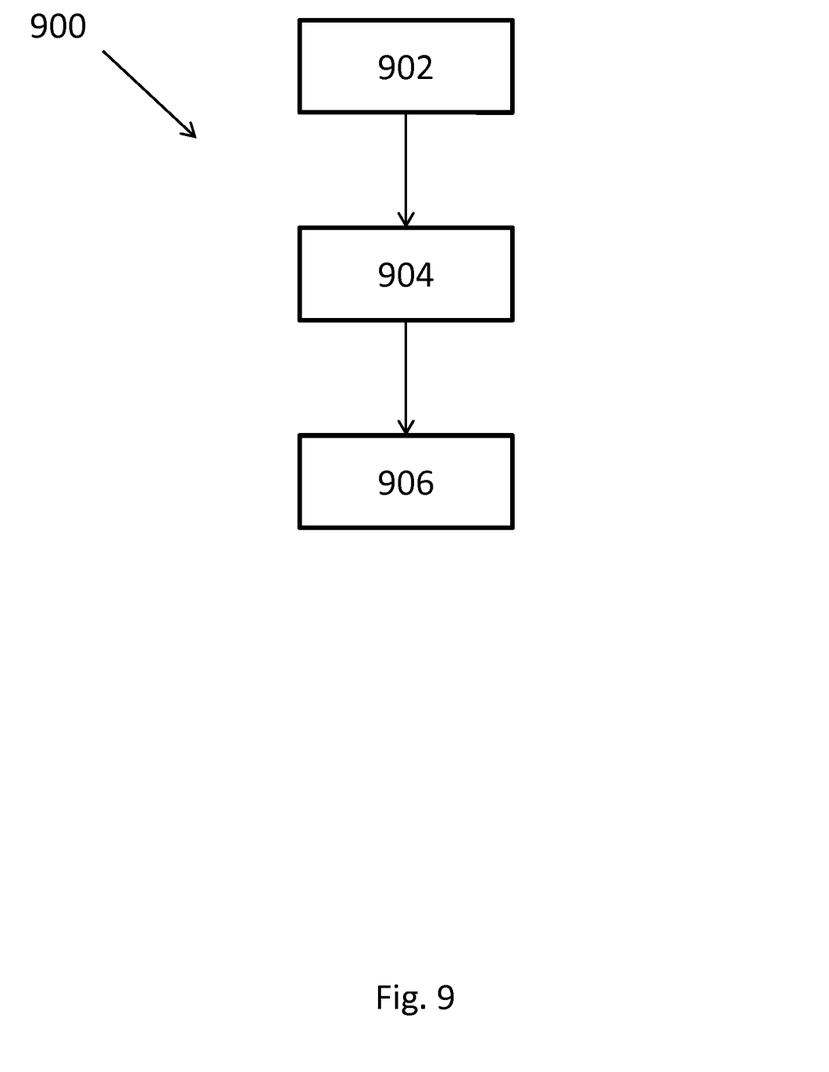
FIG. 9 shows a flowchart of a method for sample collection, according to at least one embodiment of the present disclosure.

In at least one embodiment of a method 900 for storage of a biological sample is depicted in FIG. 9. In an exemplary embodiment of method 900, the method comprises the steps of coupling an exemplary card assembly 100/200 of the present disclosure to a biological sample collection apparatus capable of collecting a biological sample from a subject (exemplary coupling step 902), introducing the biological sample to a collection medium of an embodiment of a storage device (such as card assembly 100/200) of the present disclosure (exemplary introducing step 904), and optionally drying the liquid sample 906 on the storage device (exemplary drying step 906).

In at least one embodiment of the method 900 of the present disclosure, blood spots are allowed to dry while new spots are collected on the same card. Since an exemplary card 100 or 200 remains on the collection instrument 804, no additional space is required to dry blood samples, and no change in environmental conditions are encountered during the drying process in at least this embodiment of the method of the present disclosure. Further, in at least one embodiment of introducing step 902, duplicate aliquots of liquid samples can be put on the same collection medium. In at least one additional embodiment, the duplicate spots may be on opposite sides of the collection medium, or on different pieces of the collection medium should it be separated by separation element 295 or 297.

Figure 10:
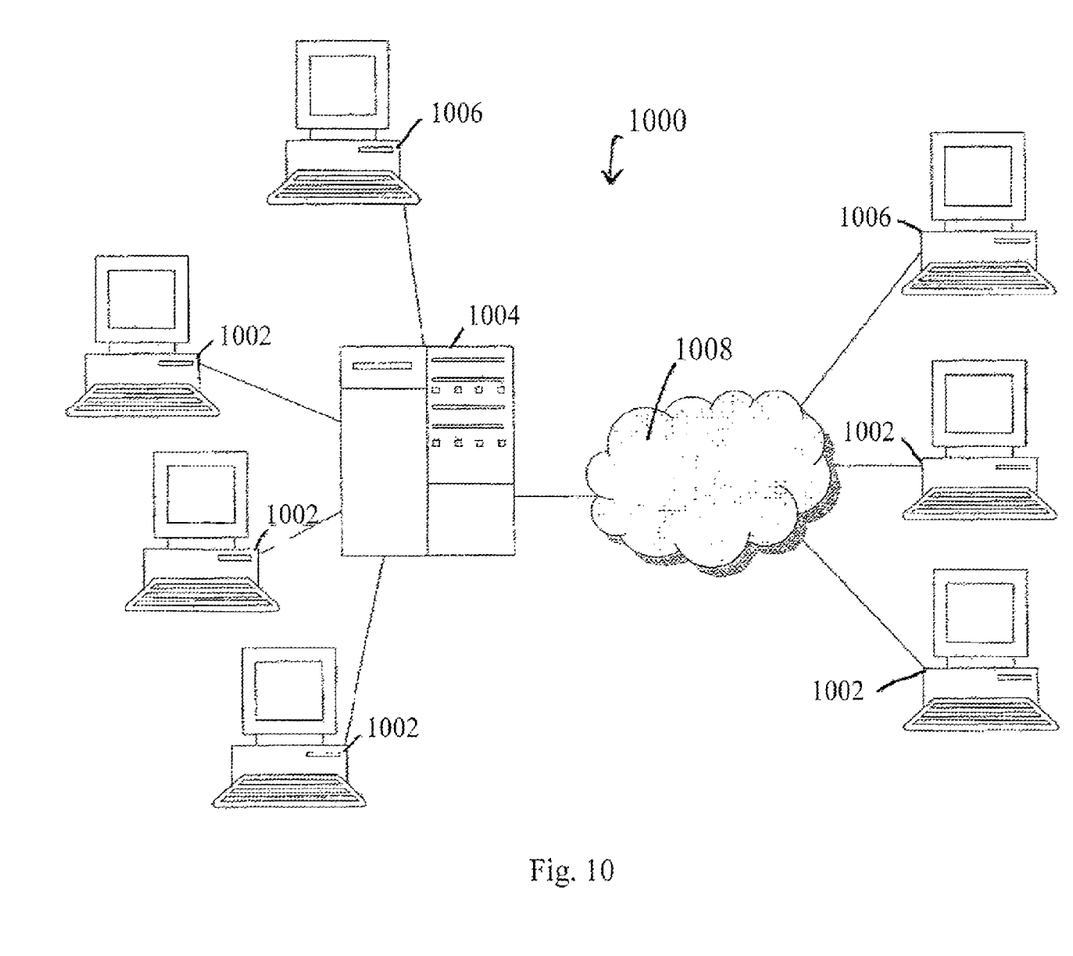
FIG. 10 shows an exemplary system framework according to an embodiment of the present disclosure.

The various systems 800 of the present disclosure may operate on a computer network having one or more of the features shown in FIG. 10. As shown in exemplary system framework 1000 shown in FIG. 10, one or more user computers 1002 may be operably connected to a system server 1004. A user computer 1002 may be a computer, computing device, or system of a type known in the art, such as a personal computer, mainframe computer, workstation, notebook computer, laptop computer, hand-held computer, wireless mobile telephone, personal digital assistant device, and the like.

One or more administrator computers 1006 may also be operably connected to system server 1004 including through a network 1008 such as the Internet. Administrator computers 1006, similar to user computers, may be computers, computing devices, or systems of a type known in the art, such as personal computers, mainframe computers, workstations, notebook computers, laptop computers, hand-held computers, wireless mobile telephones, personal digital assistant devices, and the like. In addition, user computers and administrator computers may each comprise such software (operational and application), hardware, and componentry as would occur to one of skill of the art, such as, for example, one or more microprocessors, memory, input/output devices, device controllers, and the like. User computers and administrator computers may also comprise one or more data entry means (not shown in FIG. 10) operable by a user of client computer and/or an administrator computer, such as, for example, a keyboard, keypad, pointing device, mouse, touchpad, touchscreen, microphone, and/or other data entry means known in the art. User computers and administrator computers also may comprise an audio display means (not shown in FIG. 10) such as one or more loudspeakers and/or other means known in the art for emitting an audibly perceptible output. The configuration of User computers and administrator computers in a particular implementation of one or more systems of the present disclosure is left to the discretion of the practitioner.

System server 1004 may comprise one or more server computers, computing devices, or systems of a type known in the art. System server 1004 may comprise server memory. System server 1004 may comprise one or more components of solid-state electronic memory, such as random access memory. System server 1004 may also comprise an electromagnetic memory such as one or more hard disk drives and/or one or more floppy disk drives or magnetic tape drives, and may comprise an optical memory such as a Compact Disk Read Only Memory (CD-ROM) drive. System server 1004 may further comprise such software (operational and application), hardware, and componentry as would occur to one of skill of the art, such as, for example, microprocessors, input/output devices, device controllers, video display means, and the like.

System server 1004 may comprise one or more host servers, computing devices, or computing systems configured and programmed to carry out the functions allocated to system server 1004. System server 1004 may be operated by, or under the control of, a "system operator," which may be an individual or a business entity. For purposes of clarity, System server 1004 is shown in FIG. 10 and referred to herein as a single server. System server 1004 need not, however, be a single server. System server 1004 may comprise a plurality of servers or other computing devices or systems connected by hardware and software that collectively are operable to perform the functions allocated to the various systems of present disclosure. Specifically, system server 1004 may be operable to be a web server, configured and programmed to carry out the functions allocated to a system server according to the present disclosure. Further, although user computers 1002 and administrator computers 1006 may be connected directly to system server 1004, these computers may be connected to system server 1004 through any suitable network such as network 1008. Further, in one embodiment, the users need not be provided access to system server 1004 but instead the content posts from users are made by the user(s) and saved to one or more particular locations and the posts are accessed or harvested by the administrator or system automatically.

System server 1004 may be operably connected to the various user computers 1002 and/or an administrator computer 1006 by network 1008, which in an embodiment of the present disclosure comprises the Internet, a global computer network. However, network 1008 need not comprise the Internet. Network 1008 may comprise any means for electronically interconnecting system server 1004 and a user computer 1002 and/or an administrator computer 1006. Thus, it will be appreciated by those of ordinary skill in the art that the network 1008 may comprise the Internet, the commercial telephone network, one or more local area networks, one or more wide area networks, one or more wireless communications networks, coaxial cable, fiber optic cable, twisted-pair cable, the equivalents of any of the foregoing, or the combination of any two or more of the foregoing. In an embodiment where system server 1004 and user computer 1002 and/or an administrator computer 1006 comprise a single computing device operable to perform the functions delegated to both system server 1004 and user computer 1002 and/or an administrator computer 1006 according to the present disclosure, network 1008 comprises the hardware and software means interconnecting system server 1004 and user computer 1002 and/or an administrator computer 1006 within the single computing device. Network 1008 may comprise packet switched facilities, such as the Internet, circuit switched facilities, such as the public switched telephone network, radio based facilities, such as a wireless network, etc.

The various systems, methods, schema, ontologies, and architectures of the present disclosure may be used for purposes outside of the biological sample analysis field as referenced in the various embodiments cited herein. For example, the system for collecting and storing biological samples may comprise various components and relationships suitable for use in any number of areas where various experiences are utilized and processed, with feedback being fed back into system componentry to improve overall system outcomes. In addition, various components described herein may share a name (or a portion thereof) but have duplicative reference numbers, and therefore the descriptions for the various components should read in view of one another.

In addition, and regarding the various systems of the present disclosure, such systems may be operable, as desired by a user of such systems, to generate visual, electronic (video, audio, database, transcript, etc.), and/or printed reports, outputs, outcomes, and the like. Such exemplary outputs may be used for any number of purposes, and may be useful generally to "report" results, data, and/or knowledge contained within and generated from such systems. Furthermore, the disclosure of the present application further encompasses uses of the various methods, systems, architectures, etc., to perform various tasks in connection therewith.

While various embodiments of systems for collecting and storing biological samples and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A storage device for biological samples, the device comprising:
   a collection medium having a predetermined size and shape, the collection medium comprising:
      a top surface;
      a bottom surface;
      a position marker positioned proximate to an edge of the collection medium, wherein the position marker is a void containing no collection medium;
      a first central void extending through the center of the collection medium;
      at least one first alignment void; and
      at least one binding site operable to bind a biological sample;
   a protective facing substantially impermeable to the biological sample, the protective facing coupled to the top surface of the collection medium and having a size and shape substantially similar to the predetermined size and shape of the collection medium, the protective facing including:
      a second central void in the middle of the protective facing, the second central void structured and positioned so as to align with the first central void; and
      at least one second alignment void structured and positioned so as to respectively align with the at least one first alignment void in the collection medium;
   wherein the protective facing is sized and shaped to define a first facing void and a second facing void, the first facing void positioned to allow for the transfer of the biological sample through the protective facing and onto the at least one binding site of the collection medium, the second facing void positioned to expose the position marker.

2. The storage device of claim 1, wherein the at least one binding site is positioned proximate to the edge of the collection medium.

3. The storage device of claim 1, wherein the at least one binding site comprises a plurality of binding sites each positioned in a row along the edge of the collection medium.

4. The storage device of claim 1, where the collection medium further comprises a separation element operable to divide the collection medium into at least two predetermined portions.

5. The storage device of claim 4, wherein the separation element is a perforation capable of separating the collection medium into the at least two predetermined portions upon exertion of a force.

6. The storage device of claim 4, wherein the separation element is positioned so as to divide the collection medium into the at least two predetermined portions through the position marker.

7. The storage device of claim 1, wherein the biological sample is selected from the group consisting of blood, blood fractions, sweat, urine, tears and cerebral spinal fluid, or combinations thereof.

8. The storage device of claim 1, wherein the collection medium is substantially circular.

9. The storage device of claim 1, further comprising an identification marker coupled to the protective facing.

10. The storage device of claim 1, wherein the at least one first alignment void and the at least one second alignment void are structured and positioned so as to allow the passage of an alignment member.

11. The storage device of claim 10, further comprising the alignment member traversing both the at least one first alignment void and the at least one second alignment void, and securing the collection medium to the protective facing.

12. The storage device of claim 1, wherein the protective facing comprises a coupling member and the protective facing is shaped to define a coupling void capable of engaging the coupling member.

13. The storage device of claim 12, wherein the protective facing comprises a top facing and a bottom facing, the top facing shaped to define the coupling void and the bottom facing defining the coupling member;
   wherein when the collection medium is placed between the top facing and bottom facing, and the coupling void engages the coupling member, the collection medium is securably engaged to the protective facing.

14. The storage device of claim 1, wherein the protective facing is coupled to a bottom surface of the collection medium.

15. The storage device of claim 1, wherein the storage device is sized and shaped to define at least one third alignment void operable for engaging a sample collection apparatus.

16. A system for the storage of biological samples, the system comprising:
   a biological sample collection apparatus capable of collecting a biological sample from a subject; and
   a storage device capable of receiving the biological sample from the collection apparatus, the storage device comprising:
      a collection having a predetermined size and shape, the collection medium comprising:
         a top surface;
         a bottom surface;
         a position marker positioned proximate to an edge of the collection medium, wherein the position marker is a void containing no collection medium;
         a first central void extending through the center of the collection medium;
         at least one first alignment void; and
         at least one binding site operable to bind a biological sample;
      a protective facing substantially impermeable to the biological sample, the protective facing coupled to the top surface of the collection medium and having a size and shape substantially similar to the predetermined size and shape of the collection medium, the protective facing including:
         a second central void in the middle of the protective facing, the second central void structured and positioned so as to align with the first central void; and
         at least one second alignment void structured and positioned so as to respectively align with the at least one first alignment void in the collection medium;
      wherein the protective facing is sized and shaped to define a first facing void and a second facing void, the first facing void positioned to allow for the transfer of the biological sample through the protective facing and onto the at least one binding site of the collection medium, the second facing void positioned to expose the position marker.

17. The system of claim 16, wherein the at least one binding site is positioned proximate to the edge of the collection medium.

18. The system of claim 16, wherein the at least one binding site comprises a plurality of binding sites each positioned in a row along the edge of the collection medium.

19. The system of claim 16, where the collection medium further comprises a separation element operable to divide the collection medium into at least two predetermined portions.

20. The system of claim 19, wherein the separation element is a perforation capable of separating the collection medium into the at least two predetermined portions upon exertion of a force.

21. The system of claim 19, wherein the separation element is positioned so as to divide the collection medium through the position marker.

22. The system of claim 16, wherein the protective facing comprises a coupling member and the protective facing is shaped to define a coupling void capable of engaging the coupling member.

23. The system of claim 22, wherein the protective facing comprises a top facing and a bottom facing, the top facing shaped to define the coupling void and the bottom facing defining the coupling member;
    wherein when the collection medium is placed between the top facing and bottom facing, and the coupling void engages the coupling member, the collection medium is securably engaged to the protective facing.

* * * * *